Figure 1:
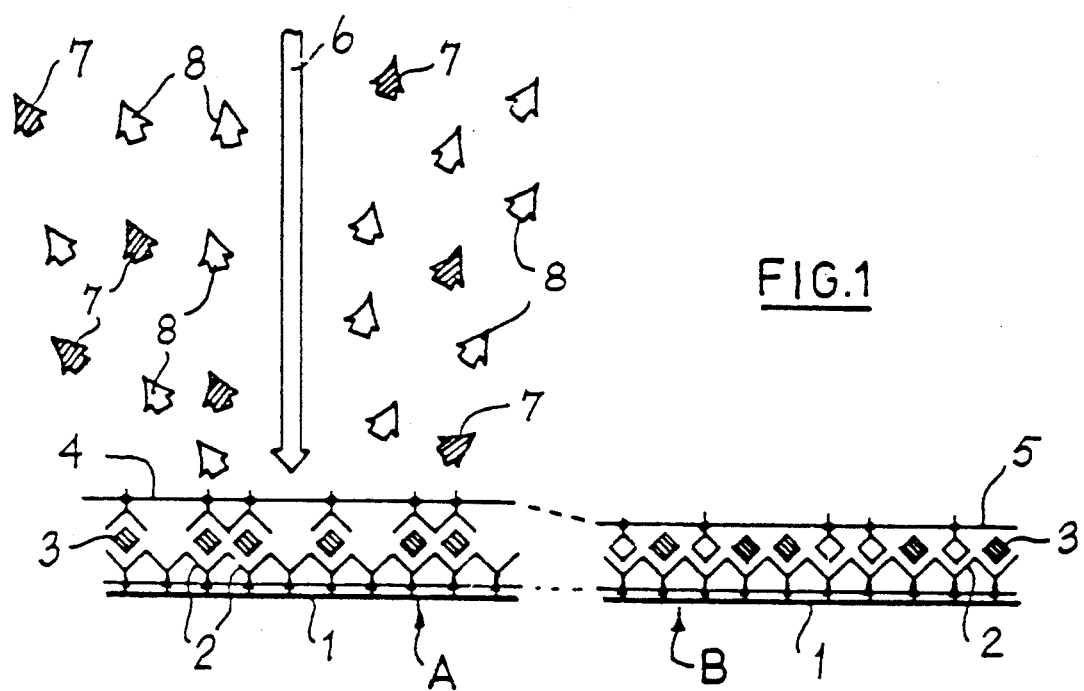

United States Patent [19]

Ekins

[11] Patent Number: 5,171,695
[45] Date of Patent: Dec. 15, 1992

[54] DETERMINATION OF ANALYTE CONCENTRATION USING TWO LABELLING MARKERS

[75] Inventor: Roger P. Ekins, London, England
[73] Assignee: Multilyte Limited, London, England
[21] Appl. No.: 317,471
[22] PCT Filed: Aug. 6, 1987
[86] PCT No.: PCT/GB87/00558
  § 371 Date: Feb. 3, 1989
  § 102(e) Date: Feb. 3, 1989
[87] PCT Pub. No.: WO88/01058
  PCT Pub. Date: Feb. 11, 1988

[30] Foreign Application Priority Data
  Aug. 6, 1986 [GB] United Kingdom ............... 8619206
  Aug. 6, 1987 [EP] European Pat. Off. ........ 87306995.9

[51] Int. Cl.$^5$ .......................................... G01N 33/566
[52] U.S. Cl. .................................... 436/501; 436/517; 436/518; 436/800; 436/808; 436/63; 436/164
[58] Field of Search ................ 436/501, 517, 518, 63, 436/800, 808, 164

[56] References Cited

FOREIGN PATENT DOCUMENTS 0026103 4/1981 European Pat. Off.
0015687 9/1981 European Pat. Off.
8002076 10/1980 World Int. Prop. O.
8401031 3/1984 World Int. Prop. O.

Primary Examiner—James C. Housel
Assistant Examiner—Lyle Alexander
Attorney, Agent, or Firm—Dann, Dorfman, Herrell and Skillman

[57] ABSTRACT

In order to measure the concentration of an analyte in a liquid sample the sample is contacted with a receptor molecule having binding sites for the analyte and labelled with a first marker, whereby a fraction of the binding sites on the receptor molecule become occupied by the analyte, the sample being contacted with such a small amount of the receptor, having regard to its affinity constant with the analyte, that only an insignificant fraction of the analyte becomes bound to the receptor. The receptor having fractionally occupied binding sites is then back-titrated by means of a back-titration technique involving a system including a second marker different from the first, and the relative strengths of the two signals produced by the two markers are measured to provide a value representative of the fractional occupancy of the binding sites on the receptor molecule by the analyte. This value is compared with one or more corresponding values obtained in the same way using one or more standard liquid samples of known analyte concentration. An analytical device suitable for use in such a method comprises an extended solid substrate (20) bearing at a plurality of spaced-apart locations (21) a plurality of different receptors (22) each having binding sites on their molecule for an analyte, the receptor at any one location having binding sites specific for an analyte different from the analyte for which the receptor at one or more other locations has specific binding sites, each of the receptors being optionally labelled with a marker. This device can be used as part of a kit for the method.

33 Claims, 1 Drawing Sheet

DETERMINATION OF ANALYTE CONCENTRATION USING TWO LABELLING MARKERS

TECHNICAL FIELD

The present invention relates to a method of measuring the concentration of analytes in liquids using two different labelling markers by immunoassay or immunometric techniques, also to an analytical device and kit.

BACKGROUND ART

It is known to measure the concentration of an analyte such as a drug or hormone in a liquid by exposing the liquid to a receptor having binding sites on its molecule for the analyte, separating the receptor containing bound analyte from the liquid, measuring a value representative of the proportion of the available binding sites on the receptor molecule that have been occupied by analyte molecules (referred to as the fractional occupancy) and comparing that value with a corresponding measured value obtained with a solution of known concentration of the analyte.

The measurement of the value in question can be achieved by a back-titration technique involving contacting the receptor molecule containing bound analyte with a labelled version of the analyte. It is also possible to use, instead of labelled analyte, another labelled material able to occupy only those of the analyte binding sites on the receptor molecule that are not actually occupied by the analyte itself. These two systems are called competitive systems because the labelled analyte or other labelled material competes with the analyte being measured to occupy binding sites on the receptor molecule. In another alternative, the back-titration technique involves contacting the receptor molecule containing bound analyte with a material able to bind with the bound analyte or with only the binding sites occupied by bound analyte, this material being itself labelled or being subsequently labelled by attachment of a labelled marker. This system is known as a non-competitive system because there is no competition for binding sites.

In both the competitive and the non-competitive system the back-titration reagent (analyte or other material) is labelled with a marker. A variety of markers have been used, for example radioactive isotopes (radioimmunoassay), enzymes, chemiluminescent substances and fluorescent markers (fluoroimmunoassay), the latter being either a conventional fluorescent material such as fluorescein or a material which becomes fluorescent only on activation and estimation by time-resolved pulse fluorescence such as a europium or other lanthanide chelate, the magnitude of the fluorescence as revealed on scanning with a high-intensity light beam of appropriate wavelength being a measure of the amount of the labelled material taken up by the receptor molecule containing bound analyte.

Hitherto known assay techniques have depended either on a precise knowledge of the total amount of the receptor present in each sample or on the knowledge that the amount of the receptor remains precisely the same from sample to sample, especially from the unknown sample to the standard samples used for calibration purposes. They have also required an exact knowledge of the total sample volume. These requirements derive from the fact that the measured signal (e.g. fluorescence) in such systems is representative of the total amount of labelled material bound and, provided that not all the labelled material has been bound (in which event the system would be unresponsive to changes in the amount of analyte present), this total amount is dependent not only on the fractional occupancy of the binding sites on the receptor molecule, but also on the amount of receptor molecule present. In short, the fluorescent signal emitted in hithertoknown fluoroimmunoassay techniques has invariably depended in a complex (and, in practice, unknown) manner on the amount of receptor molecule used in the system and on the total amount of analyte present; this implies that both the amount of receptor and the sample volume used must be carefully standardised to ensure correct estimates of the analyte concentration in the test sample, such standardisation being a characteristic and essential feature of all hitherto-known fluoroimmunoassay techniques, particularly those described as competitive as defined above. It must be particularly emphasised that, in such techniques, the fractional occupancy of the antibody by analyte (and hence the fluorescent signal emitted) is itself dependent on the amount of receptor present; for example, increasing the number of receptor molecules by a given factor also increases the number of analyte molecules which it binds, but by a very different factor, causing the fractional occupancy of the receptor to markedly change. The amount of the labelled material binding to the receptor will also increase, but likewise in a non-proportional manner.

The necessity for standardisation of the amount of receptor used (a feature of hitherto-known fluoroimmunoassay techniques shared by analogous assay methods using other markers, such as radioisotopes) is not only experimentally demonstrable, but is theoretically predictable from consideration of the Mass Action Laws governing receptor/ligand interactions. Moreover, this requirement has also long been recognised as a serious disadvantage of these techniques, causing major problems in the quality control of immunoassay systems, particularly those in which the receptor (antibody) is attached to a solid support, and where it may be technically difficult to ensure that precisely the same amount of receptor is coupled to the solid material introduced into each sample incubation mixture. In this context, it must be noted that it has not been uncommon for those practised in the art to monitor or check the amount of receptor coupled to solid supports by labelling the receptor itself (e.g. with a radioisotope) to ensure constancy of the amount so coupled. Furthermore, it has also been recognised by those practised in the art that small variations in the amount of receptor coupled could be partially corrected for if, by use of such a receptor labelling technique, the deviation from the standard amount of receptor were known. Nevertheless, because the fractional occupancy by analyte of antibody binding sites depends in a complex and, in practice, unknown manner on both the amounts of receptor and analyte present, such approximate corrections are of limited usefulness and rarely if ever applied routinely.

For example, it has been proposed in International Patent Application WO 80/02076 to improve the quality control of immunoassays by providing two separate labels, preferably fluorescent labels, in the system, one label being attached to the competing ligand (as defined above), and a second label being attached to the receptor molecule. It is stated there that direct labelling of the receptor molecule has the advantage that the receptor molecule can be quantitatively detected during an immunoassay procedure independently of quantitative detection of the labelled (competing) ligand so that the immunoassay procedure may be made self-calibrating. In accordance with the preferred form of that invention, a fluorescent label on the receptor molecule and a fluorescent label on the labelled (competing) ligand are detected quantitatively while they are bound to each other and the quantity of the analyte present in an unknown sample is determined as a function of the ratio of the quantitative measurements of the two labels.

It is evident from the disclosures in WO/80/02076 that, apart from the use of a second label, the immunoassays described are conducted in a conventional manner. In so-called "competitive immunoassays", it is usual to employ sufficient receptor to bind 30–50% of both the labelled ligand and unlabelled analyte molecules present (at unlabelled analyte concentrations approaching zero). In so-called "non-competitive" assays, even higher concentrations of receptor are conventionally used, binding close to 100% of the analyte present. Clearly, in both these circumstances, the ratio of the signals emitted by the labelled receptor and labelled back-titration marker does not remain constant if the amount of receptor varies. (For example, in a non-competitive assay design, doubling the amount of the labelled receptor will not significantly increase the amount of analyte bound; hence the ratio will roughly halve. Similar considerations apply to the competitive systems discussed in WO/80/02076.)

The disclosures in WO 80/02076 thus merely provide a crude means of approximately correcting for minor variations in the amount of receptor present in assay systems of this type as described above, and are restricted in their application to this purpose. In short, the ratio of the quantitative measurements of the two labels (labelling receptor and competing ligand respectively) can be demonstrated, both theoretically and experimentally, not generally to constitute a measure of the amount of analyte in a conventional receptor-based assay system (such as an immunoassay), and the use of this ratio as a response variable will therefore generally give rise to analyte measurements which are grossly in error. Thus, though the disclosures in WO 80/02076 offer a technique (of limited usefulness) for simultaneously monitoring (and approximately correcting for) small variations in the amount of receptor present in individual sample incubation tubes as discussed above, they do not describe the design and operation of assay systems in which the measured ratio of two labels is an accurate and reliable measure of the analyte concentration in the sample.

Furthermore it must be emphasised that even when—as is usually the case—the amount of receptor can be very accurately standardised (i.e. the amount of receptor in every incubation tube can be held constant to very close limits and in which correction for the amount of receptor present as disclosed in WO 80/02076 is neither necessary nor useful), the resulting immunoassay system will normally require "calibration" (i.e. the inclusion of sets of assay standards containing known amounts of analyte) and this is conventional in the art. Insofar as the claim made in WO 80/02076 that labelling of the receptor renders an immunoassay 'self-calibrating' possesses validity, it is only in the restricted sense that short-term variations in the efficiency of the signal detecting equipment (e.g. the radioisotope counter, fluorometer etc., depending on the label employed) can likewise be automatically corrected for (since a reduction in detection efficiency for one label would be expected to be accompanied by a roughly proportional reduction in detection efficiency for the other, causing the ratio to remain approximately constant).

Thus, in summary, the disclosure in WO 80/02076 provide at most the means of approximately correcting for a. small variations in the amount of receptor used in receptor-based assays and b. small, short term, variations in the signal detection efficiency of label-measuring equipment. These corrections are of questionable validity and restricted utility, and have not, for these reasons, been adopted in routine assay practice.

SUMMARY OF INVENTION

My present invention relates to receptor assays of completely different concept and design from those envisaged or described in WO 80/02076, and in which the fractional occupancy of the receptor is a true, accurate and reliable measure of the analyte concentration in the medium (irrespective of the total amounts of receptor and or analyte present). These systems (not referred to nor visualised in WO 80/02076) necessarily and specifically depend on measurement of the fractional analyte occupancy of the receptor, i.e. on measurement of the ratio of unoccupied (or occupied) to total receptor sites (or some essentially equivalent ratio, e.g. the unoccupied/occupied site ratio), and therefore desirably require the separate labelling of these two classes of site. I have found, inter alia, that these systems require that the relative amounts of receptor and analyte, and the affinity between them are such that the introduction of the receptor into the test sample has no significant effect on the concentration therein of the analyte.

According to the present invention, therefore, I provide a method of determining the concentration of an analyte in an unknown liquid sample comprising contacting the sample with a receptor having binding sites on its molecule for the analyte and labelled with a first marker, whereby a fraction of the binding sites on the receptor molecule become occupied by the analyte, back-titrating the receptor having fractionally occupied binding sites by means of a back-titration technique involving a system including a second marker different from the first, measuring the relative strengths of the two signals produced by the two markers to provide a value representative of the fractional occupancy of the binding sites on the receptor molecule by the analyte, and comparing that value with one or more corresponding values obtained in the same way using one or more standard liquid samples of known analyte concentration, characterised in that the unknown and standard liquid samples are each contacted with such a small amount of the receptor, having regard to its affinity constant with the analyte, that only an insignificant fraction of the analyte becomes bound to the receptor.

When I refer to an insignificant fraction of the analyte I mean a fraction sufficiently small that the errors introduced by permitting a change in the initial analyte concentration are as small as, or smaller than, the errors unavoidably introduced into the measuring procedure elsewhere by limitations in the accuracy of sample and reagent manipulation, signal measurement, standardisation, temperature variation and the like. Generally speaking, such errors customarily amount (in total) to 10% or less, and the binding of 5% or less of the total analyte in test samples would therefore be likely to cause inter-sample measurement errors arising from this particular source to contribute negligibly to the total. Nevertheless this limit can sometimes be exceeded without detriment. Ideally, however, it is preferable to minimise measurement error by reducing the amount of analyte bound to the receptor to 1-2% (or less) of the total.

Provided that only an insignificant fraction of the analyte becomes bound, I have found that the fractional occupancy, F, of the binding sites on the receptor molecule is related to the concentration of analyte in the sample by the following equation (at thermodynamic equilibrium)

$$F = \frac{K[A]}{1 + K[A]}$$

where [A] is the concentration of the analyte in the sample and K is the affinity constant of the receptor for the analyte and is a constant at a given temperature.

In the method according to the invention any of the known types of marker can be used, for example radioactive isotopes (for example radioactive iodine), chemiluminescent substances, fluorescent markers and enzymes. These may be attached to the receptor molecule and the back-titration reagent in conventional ways. Both markers will usually be of the same type, although different. The markers will be quantitatively detected in a manner appropriate to their nature, for example by counting the radioactivity of a radioactive marker or scanning a fluorescent marker with a light beam, if necessary after activation. Preferably fluorescent or potentially fluorescent markers are used. It is possible to excite the two fluorescent marker labels simultaneously by scanning with a single light beam of appropriate wavelength and to measure the relative strengths of the two fluorescent signals. This ratio is directly representative of the fractional occupancy of the binding sites of the receptor and, under the condition mentioned above, is independent of the exact amount of receptor present and of the proportion of the total amount which is utilised for the determination by scanning with the light beam. Hence there is no longer the need to use unvarying or precisely known amounts of receptor, nor for the surface density of the receptor on its substrate to be uniform.

In another aspect my invention involves the formation of labelled products as intermediates in a method according to the invention, said labelled products comprising receptor molecules labelled with a first, preferably fluorescent marker and having binding sites a proportion of which are occupied by molecules of an analyte, said proportion being fully representative of the concentration of the analyte in a sample with which the receptor molecules have been contacted because of the use of only a trace amount of the receptor relative to the analyte and a material bound either directly or indirectly to the occupied binding sites or to the unoccupied binding sites and labelled with a second, preferably fluorescent marker different from the first.

In yet another aspect my invention provides a kit for use in a method of determining the concentration of an analyte in a liquid sample, said kit comprising a solid substrate having attached thereto molecules of a receptor labelled with a first, preferably fluorescent marker and having binding sites for an analyte, the amount of receptor on the substrate being selected according to the size of the liquid sample so that only an insignificant fraction of the analyte in the sample becomes bound to the receptor, one or more standard solutions containing known concentrations of the analyte and a back-titration reagent labelled with a second, preferably fluorescent marker different from the first and able to bind directly or indirectly either with the bound analyte or with the binding sites occupied by the bound analyte or to bind with the binding sites not occupied by the bound analyte.

As a further novel analytical tool I also provide an extended solid substrate, such as a plate or rod, bearing at a plurality of spaced-apart locations a plurality of receptors each having in their molecule binding sites for an analyte, the receptor at any one location having binding sites specific for an analyte different from those on receptors at one or more other locations, each of the receptor molecules being labelled with a marker or being capable of being so labelled.

In the accompanying drawing.

Figure 2:
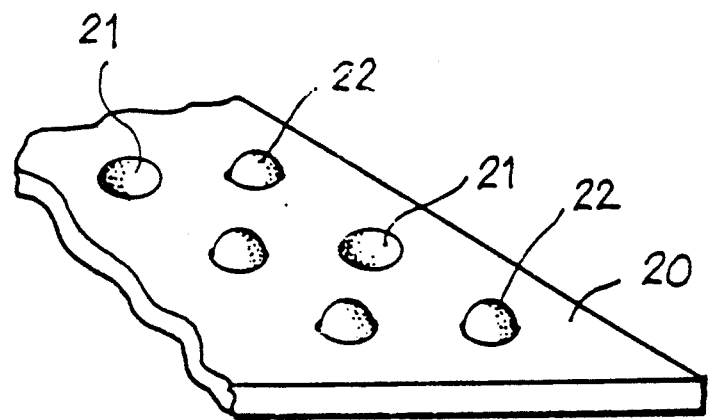

FIG. 1 illustrates schematically a competitive and non-competitive system according to the invention, and FIG. 2 is a perspective view of an analytical tool according to the invention.

Referring to FIG. 1, the diagram shows a labelled receptor 1, exemplified by a first anti-analyte antibody labelled with a first fluorophor (not shown). The receptor 1 has on its molecule binding sites 2, some of which are occupied by analyte molecules 3. In the non-competitive system A the bound analyte molecules 3 are in turn bound to a labelled material, exemplified by a second anti-analyte antibody 4 labelled with a second fluorophor (not shown). In the competitive system B the binding sites 2 on the first anti-analyte antibody 1 that are not occupied by the analyte 3 are occupied by a labelled reagent, exemplified by an anti-idiotypic antibody 5, also labelled with the second fluorophor (not shown). The complete system is scanned by a laser beam 6 and the first-fluorophor emits α-photons 7 and the second-fluorophor emits β-photons 8 differentiated from the α-photons by some property or effect. Both α- and β-photon signals will be affected equally by changes in the total amount or surface density of the first anti-analyte antibody present, provided that the fractional occupancy of binding sites is unchanged, but only the α-photon signal will be affected by changes in the fractional occupancy of the binding sites by the analyte, being increased with increasing occupancy in the non-competitive system but decreased with increasing occupancy in the competitive system. Thus, the ratio of the two signals is dependent on the fractional occupancy but not on the total amount of the first anti-analyte antibody.

My invention can be used for the estimation of any analyte for which a receptor having appropriate binding sites in its molecule is known or can be produced. It may particularly be used to estimate accurately concentrations in the picomolar or nanomolar ranges as well as higher concentrations in the micromolar range, e.g. $10^{-9}$ to $10^{-5}$ molar. Analytes that can be estimated in this way include hormones such as thyroid hormones or steroid hormones, e.g. cortisol, vitamins, proteins and protein hormones such as insulin and gonadotrophins, viruses, drugs, poisons and other normal or abnormal components of human or animal body fluid such as blood, serum, saliva, urine or the like. Examples of such analytes are listed in WO 80/02076 mentioned above, and their concentrations may be measured by the process of the present invention. Trace contaminants such as toxins, foreign proteins and the like in foodstuffs and biological contaminants in water and other liquid media can also be estimated. The analyte to be estimated may be present in a sample in equilibrium with the same analyte reversibly bound to a binding agent, such as endogenous binding protein, the concentration of free analyte being measured by the method of the invention. Alternatively the sample can be free from reversibly bound analyte, and the invention can have greater importance for such measurements as the reversibly bound analyte is not available to dissociate and hence to buffer changes in analyte concentration due to uptake by the receptor molecule.

The receptor used will be one having binding sites on its molecule for the analyte to be estimated. These binding sites should be essentially constant in number per molecule and should thus be chemical binding sites rather than physical adsorption sites. They should also be capable of occupation solely by the analyte as compared to any other ingredient of the samples undergoing estimation and will thus preferably be specific to the analyte. Antibodies, e.g. monoclonal antibodies, are particularly preferred receptor molecules, but enzymes specific to individual analytes are other examples of receptor molecules that can be used. Antibodies to a wide variety of analytes are known or described in the literature or are commercially available and other antibodies specific to other hormones etc. can be manufactured by known techniques forming no part of this invention. To maximise the precision of measurement the receptor is preferably chosen with an affinity constant for the analyte such that between 25% and 75% of the binding sites on the receptor molecule are occupied by the analyte at its expected concentration in the unknown sample, i.e. it has an affinity constant from one third to 3 times the reciprocal of the expected analyte concentration. Affinity constants for receptors may be determined by a standard Scatchard analysis (Ann. N.Y. Sci., 51, (1949, 660).

The entities to be labelled for immunofluorometric or fluoroimmunoassay, whether antibodies (both anti-analyte and anti-idiotypic), enzymes, analytes or the like, can be labelled either with conventional fluorescent materials such as fluoroscein or with materials usable in time-resolved pulsed fluorescence such as europium and other lanthanide chelates, see for example S. Dakubu and others, "High sensitivity pulsed-light time-resolved fluoroimmunoassay" in "Practical Immunoassay" edited by W. Butt, Marcel Dekker Inc. (1984) at pages 71-101 and both types of material are within the term "fluorescent marker". Methods for labelling entities with fluorescent markers to give an appropriate (sufficiently high) specific activity (proportion of labelled molecules to total molecules or total binding sites) are known in the art and described in the literature, for example in "Alternative Immunoassays", edited by W. P. Collins, published by John Wiley & Sons Ltd., in 1985, especially Chapter 13, and in the references cited therein such as Soini E. and Hemmilaa I., "Fluoroimmunoassay: present status and key problems" Clin. Chem., 25, 353-361 (1979). European Patent Applications 2,963 and 64,484, UK Patent Specification 1,560,402 and International Patent Application WO 86/01064, for which I am a co-applicant, and the references mentioned in its text or search report, also WO 80/02076 mentioned above, are further examples of literature on the topic. Such techniques can be used for labelling the receptor molecules for use in the present invention. It is also possible to effect labelling by incorporation of a fluorescent unit into a suitable material by means of a recombinant DNA technique. As mentioned above, labelling with radioisotopic and other markers is also within the scope of the invention.

Reagents suitable for use in the back-titration technique either using a competitive system, for example with an anti-idiotypic antibody or a labelled analyte, or a non-competitive system, for example with an anti-analyte antibody, are also either known in the art or can be manufactured by conventional techniques. The reagents may themselves be labelled with a marker, preferably a fluorescent marker, again of a known or conventional type using a known or conventional technique, before use or they may be reacted in situ with a further reagent which is itself labelled with such a marker. They need not differ from the back-titration reagents used in conventional immunoassay techniques employing unlabelled receptor molecules except in so far as it is necessary, for example to ensure that when two fluorescent markers are used they emit signals which can be differentiated on scanning simultaneously with a light beam if such a technique is used. The back-titration can be performed subsequently to the separation of the unbound analyte from contact with the receptor molecules (a two-step assay) or, provided that the sample volume is known, simultaneously with contact of the unbound analyte with the receptor molecules (a one-step assay):

The signals emitted by the two markers may be signals capable of being differentiated in various alternative ways, for example by wavelength of the emitted photons, by time decay of the fluorescence in the case of time-resolved pulsed fluorescence (both or only one of the markers showing such decay), or by polarisation. The wavelengths, time-decay patterns and so forth of a variety of marker systems are already known in the literature and others can be determined by known techniques. The two markers should provide signals which are sufficiently different to enable them to be resolved by the measuring instrument. The characteristics of the fluorescent signals emitted by a variety of fluorescent markers under particular conditions are already known or described in the literature and those of others can be determined in conventional ways. Thus the selection of an appropriate pair of markers is within the competence of those skilled in the art.

Although it is in principle possible for the measurement of the ratio of the signals to be made in solution this would necessitate the complete removal of all the labelled back-titration reagent which is not bound to the labelled receptor molecule/bound analyte system, for example using an immunoadsorbent, before the measurement could be effected, and such a removal step is inconvenient. I prefer therefore that the labelled receptor molecules be bound as a monolayer to a solid substrate and be separated from the residual unbound analyte and the residual unbound labelled back-titration reaction present in the liquid(s) in which the assay is conducted before measurement of the signal ratio is undertaken. Suitable substrates are made of glass, plastics or the like and techniques for binding receptor molecules such as antibodies to such surfaces are known and can be used for the purposes of this invention, see for example U.S. Pat. Nos. 4,399,217, 4,381,291, 4,357,311, 4,343,312 and 4,260,679.

In a further related invention it is possible to bind a variety of different labelled receptor molecules at spaced-apart locations on a single extended solid substrate such as a plate or rod, e.g. of inert plastics material such as polystyrene, each of the different locations being provided with receptor molecules having binding sites for one particular analyte, so that different locations bind different analytes. Such a multi-spot device can then be used to estimate concentrations of a plurality of analytes in a single liquid sample, separate labelled back-titration reagents being provided for each different analyte such that each pair of labels is capable of being differentiated and the ratio of the strengths of the signals determined. This is of particular advantage where a liquid such as a body fluid contains or may contain several different constituents of interest and the concentration of each needs to be known. (Although the use of labelled receptor molecules facilitates the production of such a multi-spot device because the amount of receptor molecule need not then be constant from spot to spot and device to device, it would also be possible to produce such a plate by using unlabelled receptor molecules provided that the amount of receptor molecule in each spot could be accurately known by other means and/or accurately controlled so as to be constant from device to device.)

Such as analytical tool is illustrated in FIG. 2 of the accompanying drawing. Referring to that Figure, a plate 20 of rectangular or other convenient shape is made of polystyrene or other inert material. It is formed with a plurality of depressions or wells 21 each of a size to accommodate a microbead 22, likewise made of polystyrene or other inert material, suitably having a diameter of about 1 mm or less. These beads have previously been soaked in a conventional manner in solutions containing a receptor such as an antibody so as to deposit the receptor as a layer on the surface of the bead, different beads being soaked in different solutions containing different receptors, and the various receptors being chosen according to the analytes to be estimated and being optionally labelled with an appropriate marker. The microbeads 22 are retained in the walls 21 by an appropriate inert adhesive such as a conventional commercially available adhesive for polystyrene.

In use of such a device having labelled microbeads the microbeads 22 on the plate 20 are contacted with the sample containing analyte(s) to be estimated and then with appropriate back-titration reagents bearing appropriate labels followed by estimation of the relative signal strengths of the two markers. Different markers will be chosen for different beads and back-titration reagents to enable the readings for one bead to be separated from those for another or alternatively each bead will be scanned separately, the latter alternative being facilitated by the use of fluorescent or fluorogenic markers.

Such a device can be constructed in numerous other ways. For example the beads 22 could be dispensed with and the receptors applied directly to the wells 21 as solutions and optionally the solvents removed leaving solid layers. Or the beads and wells could be dispensed with and the receptors printed onto the plate surface in an appropriate manner. The plate could also be replaced by a rod or other base. The number of different receptors could be as few as 2 or considerably higher, for example 5, 10 or more, and the number of different spots with the same receptor could be one or more, the use of several spots with the same receptor providing means for checking the results from a single spot.

Instruments capable of measuring pulsed fluorescent signals from materials on a solid substrate such as a plate are known, for example as supplied by CyberFluor Inc., of Toronto, Ontario, Canada, as are instruments for measuring signals in solution. If instruments for the direct measurement of the ratio in a single step are not available it is possible, although less preferred, to measure the two signals separately and to construct a ratio from those measurements with appropriate safeguards. WO 80/02076 mentioned above describes other measuring instruments which may be used in the present invention. The scanning light beam is preferably a high-intensity monochromatic or substantially monochromatic beam, especially a laser beam. The wavelengths for the excitation of the fluorescence using the scanning light beam should be chosen according to the nature of the fluorescent markers according to known principles and it is clearly preferable for both signals to be capable of excitation by and actually to be excited by a beam of a single wavelength. Pulsed fluorescence with time-resolution is the preferred technique for at least one of the markers because it enables the background interference to be screened out more readily, but it is not an essential part of my invention. If other types of marker are used appropriate standard counting or estimating devices and methods are used instead.

Because the invention is operated using antibodies or other receptor molecules in such a small amount and of such an affinity constant for the analyte to be estimated that only an insignificant fraction (usually less than 5%, preferably less than 1%) of the total amount of analyte present in the sample becomes bound to the receptor molecules, it is unnecessary to use a sample of known volume for the concentration measurement or samples of constant volume for the calibration tests, nor need such volume be measured accurately or at all, provided that it is sufficiently large in relation to the amount of receptor that only an insignificant fraction of the analyte becomes bound to the receptor. The device can therefore be used as a probe to monitor mixed analyte concentrations in large bulks of fluid such as are found in industrial processes.

A further advantage is that, when using fluorescent markers and scanning with a light beam, the light beam need not encompass the entire spot containing the receptor molecules but can merely sample a portion of the spot because the total amounts of bound analyte and receptor molecule need not be studied.

It is also unnecessary that when using a competitive system for the back-titration the labelled anti-idiotypic antibody or other labelled back-titration reagent should occupy all the binding sites left unoccupied by the analyte, provided that it occupies a proportion of them which remains constant as between estimations using the liquid sample of unknown analyte concentration and the standards of known analyte concentration. This will in general involve the use of constant (relatively high) concentrations of anti-idiotypic antibody or other labelled back-titration reagent exposed to trace amounts of the receptor molecule/bound analyte system or the use of constant volumes as well as constant concentrations. Similar remarks apply to the reaction of the bound analyte the analyte-occupied binding sites in the non-competitive back-titration system.

The present invention can be packaged for commercial use in the estimation of analytes in hospitals and the like, in conjunction with an appropriate fluorescence-measuring instrument, in the form of a kit composed of the labelled receptor molecules on a solid substrate, standard solutions of the analyte and labelled back-titration reagents. Use of such a kit will enable the measurements to be performed routinely on suitable instruments.

The invention is further illustrated by the following Examples.

EXAMPLE 1

Illustration of basic principles of methodology in an assay of thyroxine (T4) using radiolabelled ($^{131}$I) anti-thyroxine antibody and radiolabelled ($^{125}$I) thyroxine, and of the selection of reagent concentrations to yield a valid label ratio immunoassay method.

(Antithyroxine antibody is commercially readily available, and has also been prepared in the Department of Molecular Endocrinology, the Middlesex Hospital Medical School, Mortimer Street, London, both by conventional (in vivo) immunisation techniques, and by in vitro monoclonal antibody production methods.) The antithyroxine antibody used in this Example was a specific T4 monoclonal antibody prepared by selection from a range of antibodies produced by immunisation of mice using bovine thyroglobulin as immunogen. It possesses a binding constant in the order of $10^9$ 1/M and is otherwise unexceptional in its binding characteristics. It was labelled with $^{131}$I using the conventional chloramine-T technique commonly used for the preparation of iodine-labelled antibodies and other proteins. It was subsequently coupled to a commercially available microcrystalline cellulose (Sigma-Cell Type 20) using a conventional technique (Clinica Chimica Acta. Vol. 118, (1982) pp. 129–134).

High specific activity $^{125}$I labelled thyroxine was purchased from Amersham International, Amersham, Berks.

T4 present in serum (1 ml) was extracted using a commercially available anion exchange resin (BioRad AG1x2 (400–600 mesh) as a column) and eluted with 70% acetic acid after washing (see Endocrinology, 117 (1985), page 1890). Recovery experiments (using negligible trace quantities of $^{125}$I labelled T4 initially added to the test serum) revealed total recoveries in the order of 70%. Test serum eluates were each redissolved in a standard Hepes buffer (50 mls) to yield T4 solutions calculated as lying in the concentration range 0.5–1.5 ng/ml (i.e. in the order of $10^{-9}$ M/l. Standard T4 solutions were made up by appropriate dilution of a stock solution of T4 in Hepes buffer to yield a range of T4 concentrations lying between 0 and 10 ng/ml.

In an initial series of experiments, different amounts of solid-phased $^{131}$I-labelled antibody were incubated together with 1 ml volumes of standard solutions containing T4 together with tracer amounts of $^{125}$I-labelled T4, the combined T4 concentration equalling 0.1 ng/ml, for incubation times varying from 10 minutes to 8 hours. Following incubation, the solid-phased antibody was separated by centrifugation, washed, and the adsorbed $^{125}$I-labelled T4 counted using a dual channel gamma counter, and conventional calculation methods, to distinguish $^{125}$I activity per se. Curves relating antibody-adsorbed $^{125}$I activity to incubation time and amount of labelled antibody were drawn. On the basis of this data, an amount of antibody and an incubation time were selected such that in the order of 5% of the total T4 present in the incubation mixture (i.e. approximately 5 pg, yielding approximately 1000 $^{125}$I cts/min) was calculated as being adsorbed by the antibody (i.e. an amount of antibody yielding approximately 200 $^{131}$I cts/min and a total incubation time of 4 hours). It was confirmed that under these conditions: a. increasing or decreasing the amount of antibody used by factors of 2 did not significantly (i.e. within 2%) change the $^{125}$I/$^{131}$I ratio; b. increasing the volume of the standard solution used did not affect the $^{125}$I/$^{131}$I ratio.

Using this standard amount of antibody, assay calibration was effected in the following manner. The standard amount of antibody was incubated with 1 ml volumes of the standard T4 concentrations described above for 4 hours. The solid phased antibody was then, in each case, isolated by centrifugation, briefly washed with buffer and reincubated with 3 ml volumes of a standard solution of $^{125}$I-labelled T4 containing approximately 1 ng/ml T4 for a further period of 4 hours. The solid phased antibody was again, in each case, isolated by centrifugation, carefully washed 4 times to remove all remaining $^{125}$I-labelled T4 solution, and the $^{125}$I/$^{131}$I ratio corresponding to each standard T4 concentration measured. Since a standard amount of antibody (yielding approximately 200 $^{131}$I cts/min) had been used in this series, the $^{131}$I count was essentially constant in each case; the $^{125}$I count nevertheless varied from approximately 2000 cts/min in the case of the zero T4 concentration standard to approximately 200 cts/min in the case of the 10 ng/ml T4 standard (i.e. a $^{125}$I/$^{131}$I ratio ranging 10:1 to 1:1). It was again confirmed, in a further series of experiments, a. that five-fold variations in the amount of solid phased antibody used did not affect the shape and position of the dose response curve, and b. that comparable factorial increases in the volumes of the standard T4 solutions likewise did not affect the curve. These results demonstrated the system to be independent of sample volume and antibody concentration. The system was subsequently employed to assay the T4 extracts obtained as described above, the $^{125}$I/$^{131}$I ratio values for the unknowns being compared with the standard curve in the usual way, and the results compared with those obtained in a conventional T4 assay procedure. Results were closely comparable, agreement being usually within 5%, and rarely worse than 10%.

EXAMPLE 2

Establishment of a dual fluorescence T4 assay method.

Example 1 illustrates the route taken to establish a valid "dual label ratio" competitive immunoassay method. Substitution of a fluorescein label for $^{125}$I for labelling T4, and of a rhodamine label for $^{131}$I to label anti-T4 antibody have enabled establishment of an analogous dual-fluorescence ratio immunoassay method. The labelling of antibody and T4 with these fluorescent labels was effected by conventional methods "Immunochemistry in Practice", A Johnston and R Thorpe, Blackwell Scientific Pub (1982). However, in order to assist in selection of the correct reagent concentrations, certain experiments were conducted using dual-labelled antibody (i.e. labelled with $^{133}$I and rhodamine), and dual labelled T4 (i.e. labelled with $^{125}$I and fluorescein). Furthermore, antibody was coated (by adsorption) onto small polystyrene discs, rather than covalently linked to microcellulose as described in Example 1, using a well-known technique for coating polystyrene. In this example, the T4 concentration present in the unknown samples was determined from the rhodamine/fluorescein fluorescence ratio using a Perkin Elmer Type LF-5 luminescence spectrometer (fluorimeter) to measure the fluorescence signals sequentially. The results thus obtained were again compared with those relying on measurements of the isotope ratio as described in Example 1 and with a conventional T4 assay procedure, and again satisfactory agreement obtained.

EXAMPLE 3

Establishment of a dual fluorescence T4 assay method involving time-resolved pulse fluorescence.

Instead of labelling the T4 and anti-T4 antibody with fluorescein and rhodamine as in Example 2, they were labelled respectively with terbium and europium chelates with EDTA (ethylene diamine tetraacetic acid) coupled onto the antibody in a known manner. The signal ratio was measured by known pulsed-light fluorescence techniques using a known time-resolving fluorimeter, and the results obtained with the unknown sample compared with the calibration curve obtained with standard solutions. Again satisfactory agreement was obtained with results obtained by other methods.

EXAMPLE 4

A kit for use in the estimation of RSH (thyrotrophin) according to the invention is composed of the following components:

(a) A monoclonal anti-TSH antibody commercially available from the Department of Endocrinology, the Middlesex Hospital Medical School, Mortimer Street, London, is immobilised on a solid plate and labelled with fluorescein.

(b) Standard solutions contain 0.2, 1.0, 5.0, 20.0 and 100 micro-international units of TSH per mol.

(c) The back-titration reagent is likewise a commercially available anti-TSH monoclonal antibody, this time labelled with a europium (III) chelate with cupric trifluoroacetylacetone and formaldehyde in a manner similar to that proposed in published International Patent Application WO 86/01604. The first antibody is permanently fluorescent and the second is capable of estimation by time-resolved pulse fluorescence.

Such a kit can be used for the estimation of TSH by a similar procedure to that described in Examples 1-3 above, the amount of anti-TSH antibody and the size of the sample containing TSH being chosen relative to one another so that about 5% or less of the TSH in the sample is bound to the anti-TSH antibody on the plate. The back-titration involves a non-competitive system rather than a competitive system but is in principle the same.

I claim:

1. A method of determining the concentration of an analyte in an unknown liquid sample comprising contacting the sample with a receptor molecule having binding sites for the analyte and labelled with a first marker, whereby a fraction of the binding sites on the receptor molecule become occupied by the analyte, back-titrating the receptor having fractionally occupied binding sites by means of a back-titration technique involving a system including a second marker different from the first, measuring the relative strengths of the two signals produced by the two markers to provide a value representative of the fractional occupancy of the binding sites on the receptor molecule by the analyte, and comparing that value with one or more corresponding values obtained in the same way using one or more standard liquid samples of known analyte concentration, wherein the unknown and standard liquid samples are each contacted with such a small amount of the receptor, having regard to its affinity constant with the analyte, that only an insignificant fraction of the analyte becomes bound to the receptor, and wherein the amount of receptor contacted with said unknown liquid sample is different from the amount of receptor contacted with at least one of said standard liquid samples, or the amount of receptor contacted with one of said standard liquid samples is different from the amount of receptor contacted with said unknown sample or at least one of the other standard liquid samples.

2. A method as claimed in claim 1, wherein the back-titration technique involves a competitive system including a back-titration reagent selected from the analyte labelled with a marker and another material able to occupy only the unoccupied analyte binding sites on the receptor molecule and labelled with a marker.

3. A method as claimed in claim 2, wherein the insignificant fraction is less than 2% of the total amount of the analyte present.

4. A method as claimed in claim 2, wherein the receptor is an antibody for the analyte.

5. A method as claimed in claim 2, wherein the analyte is a hormone.

6. A method as claimed in claim 2, wherein the sample containing the analyte does not contain the analyte reversibly bound to a binding agent.

7. A method as claimed in claim 1, wherein the back-titration technique involves a non-competitive system including a back-titration reagent which is able to bind with the bound analyte or only with the receptor molecule binding sites occupied by the bound analyte and which is already labelled or is subsequently labelled with a marker.

8. A method as claimed in claim 7, wherein the insignificant fraction is less than 2% of the total amount of the analyte present.

9. A method as claimed in claim 7, wherein the receptor is an antibody for the analyte.

10. A method as claimed in claim 7, wherein the analyte is a hormone.

11. A method as claimed in claim 7, wherein the sample containing the analyte does not contain the analyte reversibly bound to a binding agent.

12. A method as claimed in claim 1, wherein the markers are fluorescent markers.

13. A method as claimed in claim 12, wherein the markers are different lanthanide chelate becoming fluorescent only on activation and the fluorescence is estimated by time-resolved pulse fluorescence involving scanning with a high-intensity light beam.

14. A method as claimed in claim 12, wherein the back-titration technique involves a competitive system including a back-titration reagent selected from the analyte labelled with a marker and another material able to occupy only the unoccupied analyte binding sites on the receptor molecule and labelled with a marker.

15. A method as claimed in claim 14, wherein the markers are different lanthanide chelate becoming fluorescent only on activation and the fluorescence is estimated by time-resolved pulse fluorescence involving scanning with a high-intensity light beam.

16. A method as claimed in claim 14, wherein the insignificant fraction is less than 2% of the total amount of the analyte present.

17. A method as claimed in claim 16 wherein the markers are different lanthanide chelate becoming fluorescent only on activation and the fluorescence is estimated by time-resolved pulse fluorescence involving scanning with a high-intensity light beam.

18. A method as claimed in claim 14, wherein the receptor is an antibody for the analyte.

19. A method as claimed in claim 18, wherein the markers are different lanthanide chelate becoming fluorescent only on activation and the fluorescence is estimated by time-resolved pulse fluorescence involving scanning with a high-intensity light beam.

20. A method as claimed in claim 14, wherein the analyte is a hormone.

21. A method as claimed in claim 20, wherein the markers are different lanthanide chelate becoming fluorescent only on activation and the fluorescence is estimated by time-resolved pulse fluorescence involving scanning with a high-intensity light beam.

22. A method as claimed in claim 14, wherein the sample containing the analyte does not contain the analyte reversibly bound to a binding agent.

23. A method as claimed in claim 22, wherein the markers are different lanthanide chelate becoming fluorescent only on activation and the fluorescence is estimated by time-resolved pulse fluorescence involving scanning with a high-intensity light beam.

24. A method as claimed in claim 12, wherein the back-titration technique involves a non-competitive system including a back-titration reagent which is able to bind with the bound analyte or only with the receptor molecule binding sites occupied by the bound analyte and which is already labelled or is subsequently labelled with a marker.

25. A method as claimed in claim 24, wherein the markers are different lanthanide chelate becoming fluorescent only on activation and the fluorescence is estimated by time-resolved pulse fluorescence involving scanning with a high-intensity light beam.

26. A method as claimed in claim 24, wherein the insignificant fraction is less than 2% of the total amount of the analyte present.

27. A method as claimed in claim 26, wherein the markers are different lanthanide chelate becoming fluorescent only on activation and the fluorescence is estimated by time-resolved pulse fluorescence involving scanning with a high-intensity light beam.

28. A method as claimed in claim 24, wherein the receptor is an antibody for the analyte.

29. A method as claimed in claim 28, wherein the markers are different lanthanide chelate becoming fluorescent only on activation and the fluorescence is estimated by time-resolved pulse fluorescence involving scanning with a high-intensity light beam.

30. A method as claimed in claim 24, wherein the analyte is a hormone.

31. A method as claimed in claim 30, wherein the markers are different lanthanide chelate becoming fluorescent only on activation and the fluorescence is estimated by time-resolved pulse fluorescence involving scanning with a high-intensity light beam.

32. A method as claimed in claim 24, wherein the sample containing the analyte does not contain the analyte reversibly bound to a binding agent.

33. A method as claimed in claim 32, wherein the markers are different lanthanide chelate becoming fluorescent only on activation and the fluorescence is estimated by time-resolved pulse fluorescence involving scanning with a high-intensity light beam.

* * * * *